US005891918A

United States Patent [19]

[11] Patent Number: 5,891,918
[45] Date of Patent: Apr. 6, 1999

Michelotti et al.

[54] METHOD FOR CONTROLLING RESISTANT FUNGI

[75] Inventors: Enrique Luis Michelotti, Fort Washington; David Hamilton Young, Ambler; James Allen Quinn, North Wales, all of Pa.

[73] Assignee: Rohm and Haas Company, Philadelphia, Pa.

[21] Appl. No.: 877,946

[22] Filed: Jun. 18, 1997

Related U.S. Application Data

[60] Provisional application No. 60/020,515 Jun. 28, 1996.

[51] Int. Cl.[6] .................... A01N 37/18

[52] U.S. Cl. .................... 514/617; 514/619; 514/621; 514/622

[58] Field of Search .................... 514/514, 617, 514/621, 622, 619

[56] References Cited

U.S. PATENT DOCUMENTS

| | | | |
|---|---|---|---|
| H811 | 8/1990 | Nasu et al. | 514/92 |
| 3,751,239 | 8/1973 | McNutty et al. | 71/118 |
| 4,822,902 | 4/1989 | Carley et al. . | |
| 4,876,264 | 10/1989 | Anthony et al. | 514/345 |
| 5,254,584 | 10/1993 | Michelotti et al. | 514/514 |
| 5,304,572 | 4/1994 | Michelotti et al. | 514/514 |

FOREIGN PATENT DOCUMENTS

| | | |
|---|---|---|
| 753258 A2 | 1/1997 | European Pat. Off. . |

*Primary Examiner*—José G. Dees
*Assistant Examiner*—Alton Pryor
*Attorney, Agent, or Firm*—Guy T. Donatiello

[57] ABSTRACT

A method for controlling phytopathogenic fungi is disclosed. The method uses a fungicidal composition which has been found to be effective against strains of fungi which are resistant to benzimidazole fungicides. When combined with one or more of benzimidazole, thiophanate, or dicarboximide fungicides, and applied to a mixed population of sensitive and resistant fungi, the fungicidal compound of the present invention is more effective against the mixed population of fungi than either of the fungicidal compounds alone.

6 Claims, No Drawings

METHOD FOR CONTROLLING RESISTANT FUNGI

This application claims benefit of U.S. Provisional Application No. 60/020,515 filed Jun. 28, 1996.

The present invention relates to a method for controlling resistant fungi. In particular, the present invention relates to a method for controlling fungi which have become resistant to benzimidazole or thiophanate fungicides. The method uses fungicidal compositions known as N-acetonylbenzamides.

Benzimidazole and thiophanate fungicides such as benomyl (methyl 1-(butylcarbamoyl)benzimidazol-2-ylcarbamate), fuberidazole (2-(2'-furyl)benzimidazole), thiabendazole (2-(4-thiazolyl)benzimidazole), carbendazim (methyl benzimidazol-2-ylcarbamate), thiophanate-methyl (1,2-bis(3-methoxycarbonyl-2-thioureido)benzene), thiophanate (1,2-bis(3-ethoxycarbonyl-2-thioureido) benzene), 2-(O,S-dimethylphosphorylamino)-1-(3'-methoxycarbonyl-2'-thioureido)benzene, and 2-(O,O-dimethylthiophosphorylamino)-1-(3'-methoxycarbonyl-2'-thioureido)benzene are known in the art for use against plant pathogenic fungi. However, use of benzimidazole and thiophanate fungicides over a period of time can result in the development of fungal strains having reduced sensitivity to these fungicides, whereby the fungicides are much less effective in controlling a particular fungal disease. Such "resistant" fungi when isolated as pure cultures typically are from 10-fold to >1,000-fold less sensitive to benzimidazoles and thiophanates than fungi from locations which have not been exposed to these fungicides. Moreover, fungi which develop reduced sensitivity to one benzimidazole or thiophanate fungicide frequently also show reduced sensitivity to other benzimidazole or thiophanate fungicides.

Use of dicarboximide fungicides such as procymidone (3-(3',5'-dichlorophenyl)-1,2-dimethylcyclopropane-1,2-dicarboximide), iprodione (3-(3'5'-dichlorophenyl)-1-isopropylcarbamoylimidazolidin-2,4-dione), vinclozolin (3-(3',5'-(dichlorophenyl)-5-methyl-5-vinyloxazolidin-2,4-dione) and chlozolinate (ethyl (RS)-3-(3',5'-dichlorophenyl) -5-methyl-2,4-dioxooxazolidine-5-carboxylate) can also result in the development of fungal strains with reduced sensitivity to dicarboximides. "Dicarboximide-resistant" fungi typically are from 5-fold to 200-fold less sensitive to dicarboximides than are fungi from locations which have not been exposed to dicarboximides. In the case of certain plant diseases such as *Botrytis cinerea* and *Monilinia fructicola*, where dicarboximides along with benzimidazole or thiophanate fungicides have been used for a period of time, fungal strains with reduced sensitivity both to dicarboximides and to benzimidazole or thiophanate fungicides can develop.

Therefore there is a continuing need for fungitoxic compounds which are effective in controlling resistant fungi.

It has been surprisingly found that N-acetonylbenzamides are particularly effective against benzimidazole-resistant fungi. It has been further discovered that a mixture of one or more N-acetonylbenzamides with one or more benzimidazole fungicides provides a fungitoxicity greater than does either compound alone when applied to a mixed population of benzimidazole-resistant and benzimidazole-sensitive fungi. A mixture of one or more N-acetonylbenzamides with one or more thiophanate fungicides provides a fungitoxicity greater than does either compound alone when applied to a mixed population of thiophanate-resistant and thiophanate-sensitive fungi. In addition, a mixture of one or more N-acetonylbenzamides with one or more dicarboximide fungicides provides a fungitoxicity greater than does either compound alone when applied to a mixed population containing one or more strains which are resistant to both benzimidazoles and dicarboximides and one or more strains which are sensitive to both benzimidazoles and dicarboximides.

N-acetonylbenzamides are known in the art; see, for example, U.S. Pat. No. 4,822,902.

The present invention provides a method for controlling resistant fungi by applying to plant foliage, plant seed, or a growth medium therefor, a fungicidally effective amount of at least one compound having the structural formula:

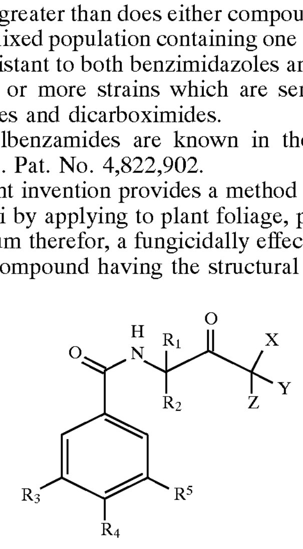

wherein:

$R_3$, $R_4$ and $R_5$ are each independently hydrogen,carboxyl, halo, $(C_1–C_6)$alkyl, $(C_2–C_6)$ alkenyl, $(C_2–C_6)$ alkynyl, $(C_1–C_6)$alkoxy, $(C_1–C_6)$haloalkyl, $(C_1–C_6)$haloalkoxy, cyano, $NO_2$, $CONR_{11}R_{12}$, $CR_6{=}NOR_7$; $NHCOOR_6$ or $NR_8R_9$ where $R_8$ and $R_9$ are each independently hydrogen, $(C_1–C_6)$alkyl, or $(C_1–C_6)$alkylcarbonyl;

$R_6$ is hydrogen, $(C_1–C_6)$alkyl, $(C_2–C_6)$alkenyl, or $(C_2–C_6)$alkynyl;

$R_7$ is hydrogen, $(C_1–C_6)$alkyl, $(C_2–C_6)$alkenyl, $(C_2–C_6)$ alkynyl, or $(C_1–C_6)$alkylcarbonyloxy$(C_1–C_4)$ alkyl;

$R_1$, $R_2$, $R_{11}$ and $R_{12}$ are each independently hydrogen, $(C_1–C_6)$alkyl, $(C_1–C_6)$haloalkyl, $(C_2–C_6)$alkenyl, or $(C_2–C_6)$alkynyl, provided that $R_{11}$ and $R_2$ are not both hydrogen; and X, Y and Z are each independently hydrogen, halo, thiocyano, isothiocyano, cyano and $(C_1–C_6)$ alkylsulfonyloxy, provided X, Y and Z are not all hydrogen.

A second aspect of the present invention is a method for controlling mixed strains of resistant and sensitive fungi by applying a fungicidal composition including at least one first compound having the chemical structure (1) and at least one second fungicide.

A further aspect of the present invention is a method for controlling mixed strains of resistant and sensitive fungi by applying a fungicidal composition including at least one first compound having the chemical structure (1) and at least one second fungicide, wherein the second fungicide is selected from: benzimidazoles, thiophanates, and dicarboximides.

The enantiomers, metal salts and complexes and agronomically acceptable salts of N-acetonylbenzamides having the structure (1) are also within the scope of compounds useful in the method of present invention. When used herein to refer to the compounds used in the method of the present invention, the term "N-acetonylbenzamides" is intended to include such salts.

As used herein, the term "$(C_1–C_6)$alkyl" means a straight or branched alkyl group having one to six carbon atoms per group and includes methyl, ethyl, n-propyl, isopropyl, n-butyl, isobutyl, sec-butyl and tert-butyl.

The term "$(C_2–C_6)$alkenyl" means a straight or branched alkenyl group having two to six carbon atoms per group, such as, for example, ethenyl, 2-propenyl, 2-butenyl, 1-methylethenyl, 2-methyl-2-propenyl.

The term "($C_2$–$C_6$)alkynyl" means a straight or branched alkynyl group having from two to six carbons per group, such as, for example, ethynyl, 2-propynyl, 2-butynyl.

The term "halo" is meant to include chloro, fluoro, bromo and iodo.

The term "($C_1$–$C_6$)alkoxy" means a straight or branched alkoxy group having one to six carbon atoms per group, such as, for example, methoxy, ethoxy, propoxy, isopropoxy, butoxy, isobutoxy, sec-butoxy and tert-butoxy.

The term "($C_1$–$C_6$)alkylcarbonyl" includes, for example, methyl carbonyl and butyl carbonyl.

The term "($C_1$–$C_6$)alkylcarbonyloxy($C_1$–$C_6$)alkyl" includes, for example, methylcarbonyloxymethyl, methylcarbonyloxyethyl, methylcarbonyloxypropyl, methylcarbonyloxybutyl, ethylcarbonyloxymethyl, ethylcarbonyloxyethyl, ethylcarbonyloxypropyl, ethylcarbonyloxybutyl, propylcarbonyloxyethyl, propylcarbonyloxypropyl, butylcarbonyloxyethyl, and butylcarbonyloxybutyl.

The term "($C_1$–$C_6$)alkylsulfonyloxy" includes, for example, methylsulfonyloxy, ethylsulfonyloxy, propylsulfonyloxy, and butylsulfonyloxy.

The term "cyano" means a group having the structural formula —CN.

The term means a group having the structural formula —SCN.

The term "isothiocyano" means a group having the structural formula —NCS.

The term "carboxyl" means a group having the structural formula —COOH.

Agronomically acceptable salts include, for example, metal salts such as sodium, potassium, calcium and magnesium salts; ammonium salts such as isopropyl ammonium salts; and trialkylsulfonium salts such as triethylsulfonium salts.

In a preferred embodiment, $R_3$ and $R_5$ are each independently chloro, fluoro, bromo, or $CR_6$=$NOR_7$; $R_4$ is hydrogen, ($C_1$–$C_4$)alkyl, ($C_1$–$C_4$)alkoxy, cyano, $NO_2$, $NR_8R_9$ where $R_8$ and $R_9$ are each independently hydrogen, ($C_1$–$C_4$)alkyl, or ($C_1$–$C_6$) alkylcarbonyl; X, Y and Z are each independently hydrogen, halo, cyano, thiocyano, or isothiocyano, provided that at least one of X, Y, and Z is halo, cyano, thiocyano, or isothiocyano. More preferably, X and Y are each hydrogen and Z is halo. Even more preferably, X and Y are each hydrogen and Z is chloro.

In a highly preferred embodiment, $R_3$ is chloro or bromo; $R_5$ is $CHNOCH_3$, chloro, or bromo; $R_4$ is hydrogen, $NH_2$, ($C_1$–$C_4$)alkyl, ($C_1$–$C_4$)alkoxy or cyano; $R_1$ is ethyl; $R_2$ is methyl; X and Y are each hydrogen; and Z is chloro.

Compounds useful in the method of the present invention include, for example:

N-(1-chloro-3- methylpentan-2-one-3-yl)-4-amino-3-chloro-5-methoxyiminomethyl benzamide;

N-(1-chloro-3-methylpentan-2-one-3-yl)-3,5-dichlorobenzamide;

N-(1-chloro-3-methylpentan-2-one-3-yl)-3-bromo-5-methylbenzamide;

N-(1-chloro-3-methylpentan-2-one-3-yl)-3-chloro-5-methoxyiminomethyl benzamide;

N-(1-chloro-3-methylpentan-2-one-3-yl)-3,5-dichloro-4-methylbenzamide;

N-(1,1-dibromo-3-methylpentan-2-one-3-yl)-3,5-dichlorobenzamide;

N-(1,1-dibromo-3-methylpentan-2-one-3-yl)-3,5-dichloro-4-methylbenzamide;

N-(3-thiocyano-3-methylpentan-2-one-3-yl)-3,5-dichlorobenzamide.

The N-acetonylbenzamides to be used in the method of the present invention may be prepared using conventional synthesis techniques. Synthesis steps for preparing N-acetonylbenzamides are described, for example, in U.S. Pat. No. 5,304,572 and U.S. Pat. No. 5,254,584.

The method of the present invention is useful in controlling a broad spectrum of phytopathogenic fungi, including fungi of the classes Deuteromycetes and Ascomycetes, on such crops as grapes, potatoes, tomatoes, cucumbers, peaches apples, and cereals including wheat and rice. The present method provides fungicidal activity with relatively low phytotoxicity in such applications. The method of the present invention is particularly useful in controlling phytopathogenic fungi which are resistant to benzimidazoles.

In order to obtain acceptable fungicidal activity by using the method of the present invention, a fungicidally effective amount of fungicide must be used. As used herein, a "fungicidally effective amount" is a quantity of a compound, or of a mixture of compounds, which causes a reduction of a fungus population or decreases crop damage caused by fungi as compared to a control group. A fungicidally effective amount of a particular compound for use against a particular fungus will depend upon the type of equipment employed, the method and frequency of application desired, and the diseases to be controlled, but is typically from 0.01 kilograms (kg) to 20 kg active compound per hectare. As used herein "active compound" is meant to include all fungicides when a mixture containing more than one fungicide is used. The amount of active compound then refers to the total of fungicides in the mixture.

The method of the present invention is useful for the control of phytopathogenic fungi on crops and may be used to protect seeds, soil, and/or foliage against fungi. To provide a seed protectant, the active compound is coated on seed at a dosage rate of about 0.5 grams (g) compound per 50 kg seed to about 500 g compound per 50 kg seed. To provide a soil fungicide, the active compound may be incorporated into the soil or applied to the surface of the soil at a dosage rate of about 0.5 kg compound per hectare to about 20 kg compound per hectare and preferably at a rate of about 1 kg compound per hectare to about 5 kg compound per hectare.

The method of the present invention is more effective against benzimidazole-resistant strains of fungi (strains against which the effectiveness of benzimidazoles has been reduced by a factor of from 10 to about 1000) than against benzimidazole-sensitive strains (strains from locations which have not been exposed to benzimidazoles and have therefore not developed resistance). Similarly, the method of the present invention is more effective against thiophanate-resistant strains of fungi than against thiophanate-sensitive strains.

When an N-acetonylbenzamide described herein is used in combination with certain other fungicidal compounds, surprising effectiveness against phytopathogenic fungi is observed. In particular, when one or more N-acetonylbenzamides is used with a benzimidazole or a thiophanate fungicide, on a mixed population of fungi sensitive to and fungi resistant to the benzimidazole or thiophanate fungicide, the combination of the fungicides is substantially more effective than either fungicide used alone. When one or more N-acetonylbenzamides is used in combination with a dicarboximide fungicide on a mixed population containing strains resistant to both benzimidazoles and dicarboximides, and strains sensitive to both benzimidazoles and dicarboximides, the combination is more effective against the fungi than either fungicide used alone.

Benzimidazole fungicides useful in combination with the N-acetonylbenzamides include, for example: methyl 1-(butylcarbamoyl)benzimidazol-2-ylcarbamate), 2-(2'-furyl)benzimidazole), 2-(4-thiazolyl)benzimidazole, and methyl benzimidazol-2-yl carbamate.

Thiophanates useful in combination with the N-acetonylbenzamides include, for example: 1,2-bis(3-methoxycarbonyl-2-thioureido)benzene; 1,2-bis(3-ethoxycarbonyl-2-thioureido)benzene; 2-(O,S-dimethylphosphorylamino)-1-(3'-methoxycarbonyl-2'-thioureido)benzene; and 2-(O,O-dimethylthiophosphorylamino)-1-(3'-methoxycarbonyl-2'thioureido)benzene.

Dicarboximides useful in combination with the N-acetonylbenzamides include, for example: 3-(3',5'-dichlorophenyl)-1,2-dimethylcyclopropane-1,2-dicarboximide; 3-(3',5'-dichlorophenyl)-1-isopropylcarbamoylimidazolidin-2,4-dione; 3-(3,5-dichlorophenyl)-5-methyl-5-vinyloxazolidin-2,4-dione; and ethyl(RS)-3-(3',5'-dichlorophenyl)-5-methyl-2,4-dioxooxazolidine-5-carboxylate.

The method of the present invention may employ conventional methods for the use of fungicides. In most applications a fungicide is used with an agronomically acceptable carrier. An "agronomically acceptable carrier" is a solid or liquid which is biologically, chemically and physically compatible with the fungicidal composition. Agronomically acceptable carriers suitable for use in the method of the present invention include organic solvents, and finely divided solids, both exemplified herein. The amount of carrier is not critical, and depends upon the desired method of application, the fungus or fungi to be controlled, and the chemical formula of the fungicide. In a typical composition, the amount of fungicide may range from about 1 percent to about 99 percent and the amount of carrier is from 1 percent to 99 percent, by weight, based on the total weight of all components in the fungicide. For the method of the present invention, it is preferable that the amount of fungicide be from 1 percent to 90 percent and the carrier from 10 percent to 99 percent based on the total weight of all components in the fungicidal composition.

When an N-acetonylbenzamide is used in combination with one or more other fungicides, the preferred ratio of the N-acetonylbenzamide and the one or more other fungicides is partly determined by the type of fungus which is to be controlled, and by the relative amounts of each fungicide. The amount of N-acetonylbenzamide may be from 5 weight percent to 95 weight percent, and the total amount of the one or more other fungicides, said total of one or more other fungicides also referred to herein as "second" fungicide, will be from 95 weight percent to 5 weight percent. In most cases, 50 weight percent N-acetonylbenzamide and 50 weight percent of second fungicide, also referred to as a ratio of 1:1, will be more effective than either fungicide used alone. When a carrier is employed, it is preferable that the amount of N-acetonylbenzamide be from 0.5 percent to 89.5 percent, the amount of second fungicide from 0.5 percent to 89.5 percent, and the amount of carrier from 10 percent to 99 percent, based on the total weight of carrier, N-acetonylbenzamide and second fungicide. More preferably, the amount of carrier will be from 10 percent to 99 percent, the amount of N-acetonylbenzamide will be from 4 percent to 86 percent, and the amount of second fungicide, if present, will be from 4 percent to 86 percent.

According to the method of the present invention, the fungicides may be applied to plant foliage as fingicidal sprays by methods commonly employed, such as conventional high gallonage hydraulic sprays, low-gallonage sprays, air-blast, aerial sprays and dusts. While the dilution and rate of application will depend upon the type of equipment employed, the method and frequency of application desired and diseases to be controlled, the effective amount is typically from about 0.01 kilogram (kg) compound per hectare to about 2.0 kg compound per hectare, preferably from about 0.05 kg compound per hectare to about 1.0 kg compound per hectare and more preferably from about 0.1 kg compound per hectare to about 0.5 kg compound per hectare. As used herein, the "effective amounts" of compounds refer to the total of all fungicides when a mixture is used.

For the above disclosed purposes these fungicidal compounds can be used in the technical or pure form as prepared, as solutions or as formulations. The compounds are usually taken up in a carrier or are formulated so as to render them suitable for subsequent use as fungicides. For example, the compounds can be formulated as wettable powders, dry powders, emulsifiable concentrates, dusts, granular formulations, aerosols, or flowable emulsion concentrates. In such formulations, the compounds are extended with a liquid or solid carrier and, when dried, suitable surfactants are incorporated.

Optional components, not required for fungicidal activity but useful or required for other properties, include, but are not limited to, adjuvants such as wetting agents, spreading agents, dispersing agents, stickers, adhesives and the like in accordance with agricultural practices. It is usually desirable to include such adjuvants in foliar spray formulations. Such adjuvants are commonly used in the art and a discussion of adjuvants can be found in many references, including the John W. McCutcheon, Inc. publications *McCutcheon's Emulsifiers and Detergents* and *McCutcheon's Functional Materials*, published annually by McCutcheon Division of MC Publishing Company, New Jersey.

In general, the compounds to be utilized in the method of this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5% to 50%.

For the preparation of emulsifiable concentrates, the compounds to be used according to the method of this invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75%. Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%.

Dusts are prepared by mixing the compounds of the present invention salts and complexes thereof with finely divided inert solids which can be organic or inorganic in nature. Inert materials useful for this purpose include botanical flours, silicas, silicates, carbonates and clays. One convenient method of preparing a dust is to dilute a wettable powder with a finely divided carrier. Dust concentrations containing 20% to 80% of the active ingredient are commonly made and are subsequently diluted to 1% to 10% use concentration.

The fungicidal compounds used in the method of the present invention may optionally be used in combination with other compounds having biological activity, e.g., compounds having similar or complementary fingicidal activity or compounds having herbicidal or insecticidal activity.

In particular, the person skilled in the art will recognize that the fungicidal compounds used in the method of the present invention can also be utilized in combination with other fungicidally active compounds. These include dithiocarbamates such as, for example, maneb, mancozeb, thiram, ziram, zineb and propineb; cyclic imides such as, for example, captan, captafol and folpet; inorganic or organic copper fungicides; cymoxanil, acylalanines such as, for example, metalaxyl, furalaxyl, cyprofuram, ofurace, benalaxyl and oxadixyl; chlorothalonil; fluazinam; fosetyl-aluminum; dimethomorph and flumetover; and amino acid derivatives such as, for example, valine derivatives (discussed in U.S. Pat. No. 5,453,531); methoxyacrylate fungicides such as, for example, methyl (E)-2-{2-[6-(2-cyanophenoxy)pyrimidin-4-yloxy]phenyl}-3-methoxyacrylate; propamocarb; dinocap; imazalil; sulphur; myclobutanil; indar, triforine; dodemorph; tridemorph; pyrazophos; ethirimol; fenarimol; dithianon; dodine; fenpiclonil; pyrimethanil and tin fungicides. The use of mixtures of the N-acetonylbenzamides with other fungicidally active compounds is within the scope of the method of the present invention, and may provide advantages. For example, such a mixture may exhibit a broader spectrum of antifungal activity than the N-acetonyl benzamides alone.

The following examples are provided in order to illustrate the method of the present invention.

EXAMPLE 1

Fungitoxicity of N-acetonylbenzamides against strains of fungi sensitive to and resistant to benzimidazoles and dicarboximides A dilution series of each fungicide to be tested was prepared in dimethylsulfoxide and 125 microliters ($\mu$l) of each dilution was added to 25 ml of molten growth medium to give the final concentrations of fungicide. Test compounds used are listed in Table 1.

For *Botrytis cinerea*, the growth medium consisted of 20 g malt extract, 20 g glucose, 1 g peptone and 20 g agar per liter of water. For other organisms potato dextrose agar (Difco Laboratories) was used. The medium containing test compound was poured immediately into 9 centimeter diameter petri dishes. Two replicate plates were used for each treatment. Each plate was inoculated with a 7 mm diameter plug taken from the edge of a growing fungal culture.

The sensitivity of each strain of *Botrytis cinerea* to benzimidazoles is indicated in Table 2. *Botrytis cinerea* strain 2 originated from a vineyard in which dicarboxamindes were no longer effective against grey mold, but benzimidazoles were effective. *Botrytis cinerea* strain 3 originated from a vineyard in which benzimidazoles were no longer effective, but dicarboximides were still effective. *Botrytis cinerea* strain 4 originated from a vineyard in which benzimidazoles and dicarboximides were no longer effective.

Benzimidazole-sensitive and -resistant strains of *Monilinia fructicola* (ATCC 62880 and 62879) and *Cercospora beticola* (ATCC 24888 and 24889) were obtained from the American Type Culture Collection (ATCC). Plates were incubated at 25° C. for 2 days (*Botrytis cinerea* strains), 6 days (*Monilinia fructicola* strains), 14 days (*Cercospora beticola* strains), or 28 days (*Venturia inaequalis*) then colony diameters were measured and EC50 values (defined as the amount of fungicide required to inhibit fungal growth by 50 percent) were calculated from median effect plots. (Chou, T., Journal of Theoretical Biology 59, 253 (1976)).

*Venturia inaequalis* strain 2 originated from an orchard in which benzimidazoles were no longer effective in controlling apple scab.

Results from tests of compounds 2 and 3 against benzimidazole-sensitive and benzimidazole-resistant fungal strains are shown in Table 2. Test compounds 2 and 3 are compared with the benzimidazole carbendazim. The data indicate that test compounds 2 and 3 are more effective against strains resistant to benzimidazoles than they are against strains sensitive to benzimidazoles. The data for *Botrytis cinerea* strain 4 indicate that the test compounds are more effective against strains resistant to both benzimidazoles and dicarboximides than against strains sensitive to both benzimidazoles and dicarboximides (e.g. strain 1).

TABLE 1

List of Compounds

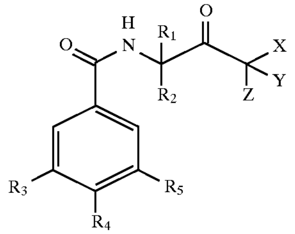

| Compound | R3 | R4 | R5 | R1 | R2 | X | Y | Z |
|---|---|---|---|---|---|---|---|---|
| 1 | Cl | NH2 | CHNOCH3 | CH3 | C2H5 | H | H | Cl |
| 2 | Cl | H | CHNOCH3 | CH3 | C2H5 | H | H | Cl |
| 3 | Cl | CH3 | Cl | CH3 | C2H5 | H | H | Cl |
| 4 | Cl | H | Cl | CH3 | C2H5 | H | H | Cl |
| 5 | Br | H | CH3 | CH3 | C2H5 | H | H | Cl |
| 6 | Cl | H | Cl | CH3 | C2H5 | H | Br | Br |

TABLE 2

Comparison of Test compounds 2 and 3 in effectiveness against benzimidazole-sensitive and benzimidazole-resistant strains

| Organism | Sensitivity to benzimidazoles | EC50 (ppm) Cmpd 3 | Cmpd 2 | Carbendazim |
|---|---|---|---|---|
| *Botrytis cinerea*, strain 1[a] | sensitive | 0.71 | 0.27 | 0.045 |
| *Botrytis cinerea*, strain 2[b] | sensitive | 1.01 | 0.36 | 0.049 |
| *Botrytis cinerea*, strain 3[a] | resistant | 0.045 | 0.031 | >50 |
| *Botrytis cinerea*, strain 4[b] | resistant | 0.043 | 0.033 | >50 |
| *Monilinia fructicola* | sensitive | 0.76 | 0.26 | <0.005 |
| *Monilinia fructicola* | resistant | 0.054 | 0.020 | >50 |
| *Cercospora beticola* | sensitive | >50 | 4.92 | 0.016 |
| *Cercospora beticola* | resistant | 0.5 | 0.19 | >50 |
| *Venturia inaequalis* strain 1 | sensitive | 0.44 | | |
| *Venturia inaequalis* strain 2 | resistant | 0.16 | | |

[a]Sensitive to dicarboximides
[b]Resistant to dicarboximides

EXAMPLE 2

Determination of Minimum Inhibitory Concentrations of N-acetonylbenzamides, alone and in combination with other fungicides, against *Botrytis cinerea*

Fungicides to be tested were dissolved in dimethylsulfoxide at 2 milligrams (mg) per milliliter (ml), and diluted into a liquid growth medium (20 grams (g) malt extract, 20 g glucose and 1 g peptone per liter of water) to give a final fungicide concentration of 100 ppm. Mixtures of fungicides at 100 ppm concentration were prepared by mixing appropriate volumes of the 100 ppm solutions of each compound. Minimum inhibitory concentration (MIC) values, defined as the minimum concentration of fungicide required to prevent visible growth, were determined using a microtiter assay with twofold serial dilutions of the prepared 100 ppm solutions in liquid growth medium. Inoculum consisted of a 1:1 mixture of *Botrytis cinerea* spores from a fungicide-sensitive strain (Strain 1, listed in Tables 2 and 3) and a fungicide-resistant strain (Strain 4, Tables 2 and 3). Each well of the microtiter plates was inoculated with 100 μl of spore suspension in water at $2\times10^4$ spores/ml. Plates were incubated at 25° C. for 4 days before determination of MIC values.

As illustrated in Table 4, combinations of N-acetonylbenzamides 1 through 6 with benzimidazole, thiophanate, or dicarboximide fungicides are more effective against the 1:1 mixture of sensitive and resistant strains than are the N-acetonylbenzamide, benzimidazole, thiophanate, or dicarboximide fungicides alone.

TABLE 4

| Compound | MIC (ppm) |
|---|---|
| 1 | 1.6 |
| 2 | 3.1 |
| 3 | 6.2 |
| 4 | >50 |
| 5 | >50 |
| 6 | 100 |
| Carbendazim | >100 |
| Benomyl | >50 |
| Thiabendazole | >50 |
| Thiophanate methyl | >50 |
| Iprodione | 12.5 |
| Vinclozolin | >100 |
| 1 + carbendazim (1:1) | 0.4 |
| 1 + benomyl (1:1) | 0.4 |
| 2 + benomyl (1:1) | 0.8 |
| 2 + thiabendzole (1:1) | 1.6 |
| 2 + carbendazim (0.2:0.8) | 3.1 |
| 2 + carbendazim (1:1) | 1.6 |
| 2 + carbendazim (0.8:0.2) | 0.8 |
| 3 + carbendazim (1:1) | 0.8 |
| 3 + thiabendazole (1:1) | 1.6 |
| 3 + iprodione (0.2:0.8) | 3.1 |
| 3 + iprodione (1:1) | 6.2 |
| 3 + iprodione (0.8:0.1) | 6.2 |
| 4 + thiophanate methyl (1:1) | 25 |
| 4 + vinvlozolin (1:1) | 6.2 |
| 4 + benomyl (0.05:0.95) | 50 |
| 4 + benomyl (1:1) | 12.5 |
| 4 + benomyl (0.95:0.05) | 6.2 |
| 5 + thiophanate methyl (1:1) | 50 |
| 5 + vinclozolin (1:1) | 12.5 |
| 6 + vinclozolin (1:1) | 50 |
| 6 + vinclozolin (0.75:0.25) | 25 |
| 6 + carbendazim (1:1) | 50 |
| 6 + carbendazim (0.95:0.05) | 25 |

What is claimed is:

1. A method for controlling benzimidazole resistant fungi comprising applying to plant foliage, plant seed, or a growth medium therefor, a fungicidal composition comprising a fungicidally effective amount of at least one N-acetonylbenzamide having the structural formula:

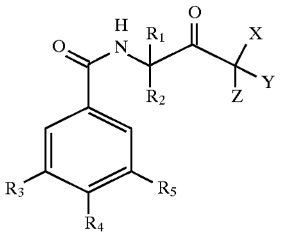

(1)

$R_3$, $R_4$ and $R_5$ are each independently selected from the group consisting of hydrogen, carboxyl, halo, $(C_1–C_6)$ alkyl, $(C_2–C_6)$alkenyl, $(C_2–C_6)$alkynyl, $(C_1–C_6)$ alkoxy, $(C_1–C_6)$haloalkyl, $(C_1–C_6)$haloalkoxy, cyano, $NO_2$, $CONR_{11}R_{12}$, $CR_6{=}NOR_7$; $NHCOOR_6$ or $NR_8R_9$ where $R_8$ and $R_9$ are each independently hydrogen, $(C_1–C_6)$alkyl, or $(C_1–C_6)$alkylcarbonyl;

$R_6$ is selected from the group consisting of hydrogen, $(C_1–C_6)$alkyl, $(C_2–C_6)$alkenyl, or $(C_2–C_6)$alkynyl;

$R_7$ is selected from the group consisting of hydrogen, $(C_1–C_6)$alkyl, $(C_2–C_6)$alkenyl, $(C_2–C_6)$alkynyl, or $(C_1–C_6)$alkylcarbonyloxy$(C_1–C_4)$alkyl;

$R_1$, $R_2$, $R_{11}$ and $R_{12}$ are each independently selected from the group consisting of hydrogen, $(C_1–C_6)$alkyl, $(C_1–C_6)$haloalkyl, $(C_2–C_6)$alkenyl, or $(C_2–C_6)$alkynyl, provided that $R_1$ and $R_2$ are not both hydrogen; and X, Y and Z are each independently hydrogen, halo, thiocyano, isothiocyano, cyano and $(C_1–C_6)$ alkylsulfonyloxy, provided X, Y and Z are not all hydrogen.

2. The method of claim 1 wherein said fungicidal composition comprises from 1 percent to 90 percent of said N-acetonylbenzamide and from 90 percent to 10 percent of an agronomically acceptable carrier.

3. The method of claim 1 wherein said fungicidal composition comprises from 0.5 percent to 89.5 percent of said N-acetonylbenzamide, from 10 percent to 99 percent of an agronomically acceptable carrier, and from 0.5 percent to 89.5 percent of at least one fungicide selected from the group consisting of benzimidazoles, thiophanates, and dicarboximides.

4. The method of claim 1 wherein: $R_3$ and $R_5$ are each independently selected from the group consisting of chloro, fluoro, bromo, and $CR_6{=}NOR_7$ where $R_7$ is selected from the group consisting of hydrogen, $(C_1–C_6)$ alkyl, $(C_2–C_6)$ alkenyl, $(C_2–C_6)$ alkynyl, and $(C_1–C_6)$ alkylcarbonyloxy $(C_1–C_4)$ alkyl; $R_4$ is selected from the group consisting of hydrogen, $(C_1–C_4)$alkyl, $(C_1–C_4)$alkoxy, cyano, nitro and $NR_8R_9$ where $R_8$ and $R_9$ are each independently selected from the group consisting of hydrogen, $(C_1–C_6)$ alkyl, and $C_1–C_6$ alkylcarbonyl; X, Y and Z are each independently selected from the group consisting of hydrogen, halo, cyano, thiocyano, and isothiocyano, and at least one of X, Y, and Z is halo, cyano, thiocyano, or isothiocyano.

5. The method of claim 1 wherein: $R_3$ is selected from the group consisting of chloro and bromo; $R_5$ is selected from the group consisting of $CHNOCH_3$, chloro, and bromo; $R_4$ is selected from the group consisting of hydrogen, $NH_2$, $(C1–C_4)$alkyl, (C1–C4)alkoxy and cyano; $R_1$ is ethyl; $R_2$ is methyl; X and Y are each hydrogen; and Z is chloro.

6. The method of claim 1 wherein said fungicidal composition is selected from the group consisting of:

N-(1-chloro-3-methylpentan-2-one-3-yl)-4-amino-3-chloro-5-methoxyiminomethyl benzamide;

N-(1-chloro-3-methylpentan-2-one-3-yl)-3,5-dichloro benzamide;

N-(1-chloro-3-methylpentan-2-one-3-yl)-3-bromo-5-methyl benzamide;

N-(1-chloro-3-methylpentan-2-one-3-yl)-3-chloro-5-methoxyiminomethyl benzamide;

N-(1-chloro-3-methylpentan-2-one-3-yl)-3,5-dichloro-4-methyl benzamide; and N-(1,1-dibromo-3-methylpentan-2-one-3-yl)-3,5-dichlorobenzamide.

* * * * *